United States Patent
Gradl

(10) Patent No.: US 8,273,130 B2
(45) Date of Patent: Sep. 25, 2012

(54) MAGNETICALLY MOUNTED ARTIFICIAL JOINT

(75) Inventor: Georg Gradl, Börgerende Rostock (DE)

(73) Assignee: Universität Rostock, Rostock (DE)

( * ) Notice: Subject to any disclaimer, the term of this patent is extended or adjusted under 35 U.S.C. 154(b) by 133 days.

(21) Appl. No.: 12/741,505

(22) PCT Filed: Nov. 5, 2008

(86) PCT No.: PCT/EP2008/065018
§ 371 (c)(1),
(2), (4) Date: Aug. 18, 2010

(87) PCT Pub. No.: WO2009/060007
PCT Pub. Date: May 14, 2009

(65) Prior Publication Data
US 2010/0331993 A1    Dec. 30, 2010

(30) Foreign Application Priority Data

Nov. 6, 2007  (DE) .................... 10 2007 053 362

(51) Int. Cl.
*A61F 2/30* (2006.01)
(52) U.S. Cl. ............... 623/18.12; 623/19.11; 623/22.11
(58) Field of Classification Search ............... 623/18.12
See application file for complete search history.

(56) References Cited

U.S. PATENT DOCUMENTS

| 4,024,588 | A | 5/1977 | Janssen et al. |
| 6,387,096 | B1 | 5/2002 | Hyde, Jr. |
| 2003/0187510 | A1 | 10/2003 | Hyde |
| 2005/0251080 | A1 | 11/2005 | Hyde, Jr. |
| 2006/0149386 | A1 | 7/2006 | Clarke |
| 2006/0247782 | A1 | 11/2006 | Molz, IV et al. |
| 2010/0331993 | A1 * | 12/2010 | Gradl .................... 623/23.4 |

FOREIGN PATENT DOCUMENTS

| JP | 10014957 A | 1/1998 |
| WO | 2008/057565 A2 | 5/2008 |

* cited by examiner

*Primary Examiner* — Corrine M McDermott
*Assistant Examiner* — Randy Shay
(74) *Attorney, Agent, or Firm* — Norris McLaughlin & Marcus P.A.

(57) ABSTRACT

The invention relates to a prosthesis for replacing a joint connection, wherein like magnetic fields from the condyle 10, socket 12 and joint collar 14 overlap in such a way that the repulsive forces generate a suspended state of the condyle 10 in the bearing and the damping effect is maximized. The invention is also directed to a method for replacing a bone junction in a mammal, wherein the prosthesis is fastened to the articular bone and repulsive forces generate a levitated state of the condyle 10 under load.

27 Claims, 2 Drawing Sheets

MAGNETICALLY MOUNTED ARTIFICIAL JOINT

Figure 1:
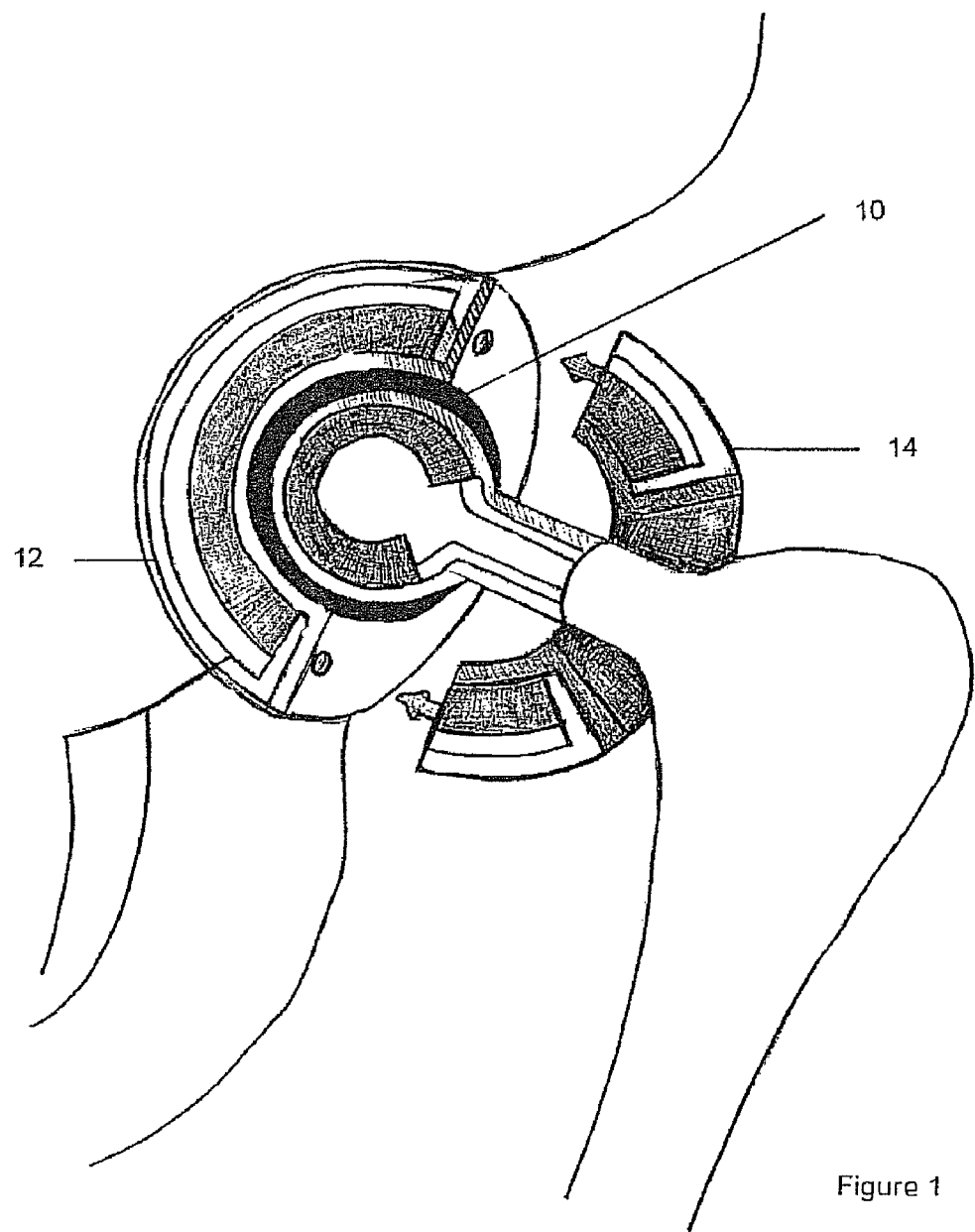

This application is a 371 application of PCT/EP2008/065018 filed Nov. 5, 2008, which claims priority to the German application 10 2007 053 362.6 filed Nov. 6, 2007.

The invention relates to a prosthesis for replacing a joint connection, wherein like magnetic fields from the condyle 10, socket 12 and joint collar 14 overlap in such a way that the repulsive forces generate a suspended state of the condyle 10 in the bearing and the damping effect is maximized. The invention is also directed to a method for replacing a bone junction in a mammal, wherein the prosthesis is fastened to the articular bone and repulsive forces generate a levitated state of the condyle 10 under load.

Joint prostheses and intervertebral disc prostheses used in orthopedics and emergency surgery suffer from the problem of abrasion in the corresponding joint components. This results in asymmetric load peaks causing more rapid loosening of the implant, or a foreign body reaction of the tissue is caused by abraded material.

There have been attempts in the prior art to reduce abrasion by using preferably hard materials forming the joint surfaces, such as ceramics, but with only limited success.

The patent application US 2006/0149386 A1 teaches a prosthetic device comprising a component for fixation in the bone and a receiving member having reservoirs and magnets, wherein either the fixation component or the receiving member has magnetic properties. The construction utilizes magnetic forces only for collecting the forming abraded debris in the magnetic reservoirs, which has to be magnetic, and preventing it from migrating into the surrounding tissue, while actual abrasion is not prevented.

Further, a prosthetic device for an intervertebral disc is known from US 2006/0247782 A1, wherein repelling magnetic fields are generated in the terminal regions, thereby keeping apart the terminal regions and generating a supporting structure for two dorsal vertebrae. The disc prosthesis has built-in electric magnets and external control and operating equipment. The magnetic forces merely effect stabilization and/or a change in length of the prosthesis, but no levitation and consequent low-wear bearing.

U.S. Pat. No. 4,024,588 discloses an artificial joint for implantation in the body, which has a head portion and a base including magnetic elements with a polarity that causes either attractive or repulsive forces. The intention of attracting magnets is to prevent dislocation of the joint, while repelling magnets are intended to achieve a damping effect as a result of the lowered effective bearing force. The construction is not capable of building up the magnetic fields required for a state of suspension because the areas involved are too small. In addition, the specified magnetic materials are not capable of building up the high permanent magnetic fields required for effective damping. If used in the present construction, a joint at rest and under no load would be pushed unnaturally far apart.

Another problem is that the interface between bone and anchoring of the artificial joint must withstand high pressures as a result of load when the patient is walking or standing. This inevitably gives rise to loosening phenomena at the interface between bone and joint over time.

The basic object of the invention is to overcome the drawbacks of abrasion and loosening identified in the prior art and develop a device that ensures virtually contact-free joint guiding.

The object of the invention is accomplished in accordance with the independent claims. The subclaims include preferred embodiments. According to the invention, a prosthesis is provided which comprises a condyle 10 and a socket 12 of complementary spatial shape and a collar 14, said condyle 10, socket 12 and collar 14 each comprising a permanent magnet layer 18 and a shielding layer 20, and said permanent magnet layers 18 of condyle 10, socket 12 and collar 14 having like polarity so that the condyle 10 and the socket 12 as well as the condyle 10 and the collar 14 are separated by a gap 24.

Surprisingly, it was found that by providing a magnetic field by means of the additional prosthetic component of collar 14, the magnetic fields generated by the permanent magnets in condyle 10, socket 12 and collar 14 can be dimensioned and arranged in such a way that an equilibrium of repulsive forces on the condyle 10 is established, thereby achieving a state of levitation (suspended state) of the condyle 10 in the bearing. As a result of magnetic joint guiding, contact-free and thus low-abrasion bearing is achieved in the joint. In addition to significantly reduced abrasion, the magnetic bearing provides damping of mechanical peak loads.

The device according to the invention comprises the three components condyle 10, socket 12 and collar 14. The condyle 10 and socket 12 are designed in such a way that their spatial structures are complementary to each other, i.e. condyle 10 and socket 12 fit into each other like key and lock. The accuracy of fit is dimensioned in such a way that no positive connection will be generated which would prevent movement, i.e. rotational and/or translational movements. A joint is formed as a result of the interaction between condyle 10 and socket 12. A "joint" is understood to be a flexible junction of two or more bones, and anatomy differentiates between diarthrosis joints (with a fluid-filled gap 24) and synarthrosis joints. It will be understood that synarthrosis joints in the meaning of the invention, e.g. junctions via fibrous cartilage, such as intervertebral discs, will likewise be replaced by a diarthrosis joint in the meaning of the invention because the inventive prosthesis will invariably generate a gap 24 as a result of the counter bearing of collar 14 required for the suspended state.

Both condyle 10 and socket 12 have additional components which permit anchoring in the corresponding articular bone.

Assembling the condyle 10 and socket 12 results in formation of a bearing surface, the size of which varies depending on the geometric design of condyle 10 and socket 12. The geometric design will follow the natural model, i.e. the existing bone junction to be replaced. In most cases the socket 12 will enclose half ±30% of the condyle surface, preferably ±10%. In a particularly preferred fashion the bearing surface is less than half the surface of the condyle 10.

On the other hand, the collar 14 is arranged such that the condyle 10 and the collar 14 form another bearing surface which differs in its location from the first bearing surface between condyle 10 and socket 12 and may vary in its spatial expanse. For this reason, the collar 14 is also referred to as counter bearing. Also, the collar 14 will be situated on the side of condyle 10 that faces away from the socket 12, i.e. is not enclosed by the latter. In other words, the collar 14 is situated behind the condyle 10, thereby at least partially facing the socket 12, and the term "partially" refers to the circumstance that parts of the collar 14 can also be arranged otherwise and/or that the bearing surface of the collar 14 is only a fraction of the bearing surface of socket 12. The collar 14 preferably represents an extension of socket 12, and both components of the prosthesis have identical shapes with equal or different volumes or different geometric shapes. Socket 12 and collar 14 are connected via a connecting element 28, preferably mechanically.

Condyle 10, socket 12 and collar 14 have a layer structure such that each comprises a permanent magnet layer 18 and a shielding layer 20. In one embodiment of the present invention, condyle 10, socket 12 and/or collar 14 additionally have a contact layer 16 and/or a support layer 22. More specifically, the contact layer 16 is positioned so as to be oriented towards the bearing surface, so that the contact layers of condyle 10 and socket 12 and/or condyle 10 and collar 14 are separated by the gap 24.

The arrangement of the layers is preferably in the order permanent magnet layer 18 and shielding layer 20. If in addition a contact layer 16 and/or a support layer 22 are present, the preferred order is contact layer 16, permanent magnet layer 18, support layer 22 and shielding layer 20. The shielding layer 20 of socket 12 and/or collar 14 may also have an outer layer 26 placed on top thereof which is tolerated by the body. Said outer layer 26 establishes contact between the socket 12 and the bone and can be regarded as additional contact layer 16 in the meaning of the invention.

In fact, the orders specified above are not absolutely compulsory, nor is the prosthesis according to the invention bound to the presence of a specific single layer because another layer may also accomplish a plurality of functions in the meaning of the invention and thus the function of a physically non-delimitable single layer. In particular, one or more layers can be integrated in another layer, or the material forming the basis of a particular layer may inherently assume the function of a number of layers of the invention, so that optional omission of layers is possible. In one embodiment of the invention the contact layer 16, the permanent magnet layer 18 and/or the shielding layer 20 are integrated in the support layer 22, preferably the permanent magnet layer 18 and the shielding layer 20. In another embodiment of the invention the permanent magnet layer 18, the shielding layer 20 and/or the support layer 22 are integrated in the contact layer 16. In a preferred fashion, such integration is only in adjacent layers without omitting a layer.

In a preferred embodiment of the prosthesis, a stable socket 12 has an outer layer 26, e.g. made of titanium, which already has a shielding effect, as a result of which outer layer 26 an additional shielding layer 20 is dispensable because the former already assumes the function of a shielding layer 20. That is, the shielding layer 20 assumes the role of a bifunctional layer rather than an independent layer. In another design of this embodiment, the permanent magnet layer 18 can be embedded in a subsequent contact layer 16 so that ultimately no more than three layers are present.

In another preferred embodiment of the prosthesis, the condyle 10 has a contact layer 16, e.g. made of a cobalt-chromium alloy, on top of which the permanent magnet layer 18 is placed without an additional support layer 22.

When using permanent magnet layers 18 having brittle material properties, stabilization by integration in the support layer 22 is possible. Alternatively or additionally, the support layer 22 may enclose the permanent magnet layer 18, in which event the support layer 22 can also serve as contact layer 16 and/or shielding layer 20, provided it has the required properties thereof. In the case of substitution of the contact layer 16 or addition as contact layer 16, the support layer 22 will have the outstanding features of body compatibility and abrasion resistance. For example, titanium is a suitable material for such a design.

In particular, the arrangement of the condyle 10 with respect to socket 12 and collar 14 is such that the layers are in reverse succession. As will be appreciated, such a configuration involves the precondition that condyle 10, socket 12 and collar 14 have the same layers, and the absence of one or more layers is not detrimental. As for the region of the bearing, the bearing surface will be formed by the contact layers 16, permanent magnet layers 18 or support layers 22, depending on which layers will constitute the outermost layer of condyle 10 or the innermost layer of socket 12 or collar 14, with two functionally identical layers being preferred. The bearing surface is preferably formed by the contact layers 16.

The contact layers 16 are made of a body-compatible and abrasion-resistant material. Depending on joint dimensioning and occurring peak loads, the maximum bearing forces may be exceeded, thus giving rise to sliding friction between condyle 10 and socket 12 with consequent abrasion. The layer thickness is 0.1 to 10 mm, preferably 1 to 3 mm, depending on the material. Preferred options are plastics, steel, titanium, ceramics or other coatings, and PE plastics and cobalt-chromium alloys are particularly preferred. More specifically, the contact layer 16 of socket 12 is made of PE plastic, ceramic or steel, while the contact layer 16 of condyle 10 is composed of ceramic or steel. The material pairs of the contact layers 16 are not particularly limited. However, the contact layer 16 of condyle 10 has a material other than that of the contact layer 16 of socket 12. In particular, there is steel or ceramic in the contact layer 16 on the condyle 10 and PE on the contact layer 16 of socket 12. One exception of this preferred embodiment are steel-steel pairs in which the same material of the contact layer is preferred. Preferred steels in the meaning of the invention are cobalt-chromium alloys.

The magnetic layer 18 is preferably situated directly below the contact layer 16. "Magnetic" in the meaning of the invention involves the presence of a magnetic field generated solely permanently by means of a permanent magnet rather than temporarily, such as by movement of electric charges. The magnetic properties of solids originate from the magnetism of atoms/ions and electrons which constitute them. A magnetic material is present in those cases where the elementary magnetic moments are oriented in such a way that mutual compensation is not complete, so that the material has macroscopic magnetization. In the meaning of the invention, "magnetic" is also understood as a generic term for the associated terms "magnetized", "paramagnetic" and "superparamagnetic", unless the specific context expressly indicates otherwise. "Magnetizable" refers to the property of a material, especially a ferromagnetic material, of exhibiting residual magnetization, or remanence, upon exposure to and subsequent removal of an external magnetic field. "Paramagnetic" describes the tendency of a substance of migrating into a magnetic field. Paramagnetic behavior is found in substances with unpaired electrons, because the spin moments of the electrons orient parallel to the external magnetic field and reinforce it. The orbital angular moments of the unpaired electrons also contribute to paramagnetism. "Superparamagnetic" indicates a particularly strong paramagnetic tendency.

The magnetic properties of condyle 10, socket 12 and collar 14 used in the prosthesis according to the invention can be furnished by magnetic materials preferably selected from a group including ceramic oxide materials, preferably barium oxide or iron oxide, or metals of subgroup VIII or an alloy thereof, preferably iron, cobalt, nickel, alloys among each other, or alloys thereof with platinum and rare earths, more preferably neodymium-iron-boron alloys or cobalt-samarium alloys.

The permanent magnet layer 18 can be made of an integral piece or a number of individual magnets which, in analogy to so-called Halbach magnets, comprise a plurality of suitably shaped and oriented individual magnets. The Halbach array has the property that the magnetic flux on one side of the configuration is almost cancelled, but reinforced on the other side.

The permanent magnet layers 18 of condyle 10, socket 12 and collar 14 have like polarity, so that repulsive forces are present between the magnetic layers 18. The repulsive forces of the magnets initially take effect in such a way that, depending on the weight of the patient, the contact pressure of the condyle 10 on the socket 12 is greatly reduced or even completely disappears. The reduction of the force on the area between condyle 10 and socket 12 results in a linear reduction of both sliding friction between the two joint components and mechanical abrasion. As a consequence, the bearing of condyle 10 in socket 12 or collar 14 is low in wear, preferably free of wear.

In one embodiment of the invention the permanent magnet layers 18 of condyle 10 and socket 12 have a flux density B of at least 0.4 Tesla. The minimum flux density depends on type and position of the joint, which determines both static load and load limit. "Static load" in the meaning of the invention is the portion of the body weight constituted by the body parts above the joint, i.e. the body parts exerting a weight force such that the joint is compressed or pulled apart, and this portion of the body weight can be distributed over several joints, thereby accordingly reducing the static load.

It will be appreciated that e.g. a knee joint will have to bear a higher static load compared to a shoulder joint, for which reason they are dimensioned for different peak load limits, which in turn requires different minimum flux densities. In the embodiment of a hip joint, the permanent magnet layers 18 of condyle 10 and socket 12 have a flux density B of 0.5 Tesla, preferably at least 0.7 Tesla, and more preferably at least 1.0 Tesla. It is also preferred that the flux densities B of the permanent magnet layers 18 of condyle 10 and socket 12 are approximately equal, the deviation preferably being 10% at maximum. It is particularly preferred that the flux densities B of the permanent magnet layers 18 of condyle 10 and socket 12 are equal. It will also be appreciated that the implementation of a particular flux density B, and thus the effective repulsive force, will depend on the geometry of the magnetic layers 18. By specifying a magnetic bearing pressure to be achieved, the design becomes independent of a particular geometry and flux density, so that any combination of bearing surface and flux density can be selected that falls within the range of a preferred bearing pressure to thereby accomplish the object of the invention. The permanent magnet layers 18 of condyle 10 and socket 12 preferably build up a maximum magnetic bearing pressure of 150,000 $N/m^2$, more preferably at least 300,000 $N/m^2$, and especially preferably at least 400,000 $N/m^2$.

The repulsive magnetic forces tend to push the condyle 10 out of the socket 12, so that a corresponding counter pressure must be built up by a counter bearing (collar 14). The permanent magnet layer 18 of collar 14 has a flux density that corresponds to at most the flux density of the permanent magnet layers 18 of condyle 10 and socket 12, with the higher flux density being the decisive one. In one embodiment of the invention the permanent magnet layer 18 of collar 14 has a flux density of 1.0 Tesla at maximum. Taking into account a minimum depth of the gap 24 between condyle 10 and socket 12 as well as the static load of the prosthesis, which corresponds to the patient's body weight, optionally portions of the body weight, the permanent magnet layer 18 of collar 14 has an at least 40% lower flux density compared to the flux density of the permanent magnet layer 18 of socket 12, preferably an at least 20% lower flux density, and more preferably an at least 10% lower flux density. It will be appreciated by those skilled in the art that instead of the flux density it is also possible to use the design of the joint, especially the bearing surface, in adjusting a suspended state.

In a preferred embodiment of the prosthesis according to the invention, the depth of the joint gap 24 under static load is between 1 and 10 mm, preferably between 3 and 6 mm, in order to achieve a damping effect under peak loads. The damping effect is characterized in that the depth of the gap 24 between condyle 10 and socket 12 will in fact decrease during loading, but will not drop to the value zero to thereby cause contact and abrasion of the contact layers 16 of condyle 10 and socket 12. The case of contact corresponds to the maximum load limit which should withstand at least 1.5 times the static load, preferably at least three times the static load, and more preferably at least five times the static load. Assuming that a patient has a body weight of 80 kg, and considering the distribution of this weight on two joints, e.g. two knee joints or hip joints, the static load of torso, thighs, arms and head to be borne by each prosthesis will be less than 40 kg, so that the maximum load limit, expressed as load mass, is at least 60 kg, preferably at least 80 kg, and more preferably at least 120 kg.

The shielding layer 20 is used to shield magnetic field lines. The static magnetic field lines produced by the permanent magnet layer 18 exert a force on charge carriers, e.g. ionic conduction of stimuli in nerve pathways, salts dissolved in body fluids, etc., in the body of a patient and, as a result, generate small electric currents. It is therefore precisely the region of the conduction systems where research on possible influences on the body should be focused, and there is only insufficient evidence relating to the effects of long-term exposure to static magnetic fields. In addition, the permanent magnets 18 act on metallic objects in the vicinity of the joint prosthesis. It is therefore essential that the magnetic fields of condyle 10, socket 12 and counter bearing 14 are directed inwardly to the bearing surface and shielded outwardly so as to comply with the limits of static magnetic fields in the surrounding tissue of a patient. Complete shielding of the magnetic field is not required, as a residual magnetic field can even stimulate bone healing. Thus, prosthesis healing into the bone is stimulated if the residual magnetic field still acts on the bone side of socket 12. The magnitude of such a stimulating residual magnetic field can be determined in routine tests by a person skilled in the art.

For persons exposed to a low-frequency magnetic field of 16⅔ Hz, the Bundesamt für Strahlenschutz in Germany has recommended an upper limit of 0.3 mT. The current limit in Germany and the recommendation of IRPA/INIRC (International Commission on Non-Ionizing Radiation Protection) for private individuals (daily, permanent residence) in 50/60 Hz fields is even only 0.1 mT, and the maximum limit for permanent working in magnetic fields is 0.5 mT. The German Arbeitskreis Elektrobiologie e.V. even calls for a limit of 0.002 mT in sleeping and resting zones. Regarding the geomagnetic field in Central Europe of about 0.045 mT on an average, a limit of from 0.1 to 0.3 mT and thus two to six times the value of the earth's magnetic field appears to be a reasonable magnitude. The shielding layer 20 must therefore shield the magnetic field of the permanent magnet layer 18 on the side facing away from gap 24 by a factor of the order of at least 1:1,000, preferably at least 1:3,000, and more preferably at least 1:10,000. Such a shielding factor can only be furnished by a combination of different shielding components which, depending on the type of shielding, are applied directly to the back of the permanent magnets 18 or at a small distance of from 1 to 3 mm.

To this end, the permanent magnets 18 must be surrounded with, among other things, a massive, so-called shielding cap of a magnetically soft material, preferably structural steel, iron, nickel, cobalt, special alloys, so-called mu-metals (or µ-metals), or combinations thereof. An alternative, or supplement, is the use of compensation magnets applied to the outside of permanent magnet layer 18 in opposite polarity thereto. It will be appreciated that both cases must be examined for possibly occurring magnetic short-circuits and the impact thereof on the inwardly directed field. The resulting residual field can be reduced using magnetically shielding metal fabric mats. The magnetic field strength decreases with the square of the distance, so that the field strength in the surrounding tissue reaches the limit value. The precise interactions between the permanent magnet layer 18 and the shielding layer 20 and the resulting magnetic fields in the interior and exterior of a prosthesis can be calculated using suitable programs.

The mechanical support layer 22 is capable of absorbing the occurring forces. The support layer 22 consists of a non-magnetic, body-compatible and ductile material such as titanium, an alloy thereof, or other composite materials. The term "composite" refers to a material constituted of two or more bonded materials which, given the case of a composite material, are bonded to each other across the entire surface and cannot be separated by hand. The composite material has different properties than the individual components thereof, to which issue the material properties and the geometry of the components are important. In particular, size effects frequently play a role. The connection is a material or positive connection or a combination of both. The components of a composite material can be composite materials themselves.

Depending on the design of the permanent magnets 18 and shielding layer 20, these layers are either directly integrated in the support layer 22 to protect them against mechanical stress, or they are placed on top of the support layer 22. In a preferred embodiment of the invention, possible materials capable of generating the required high field strengths are neodymium magnets, but these materials are usually very brittle and incapable of withstanding high mechanical stress as occurring under peak load, so that integration of the permanent magnet layer 18 and shielding layer 20 in the support layer 22 is likewise preferred. There are several possible ways of preventing breaking of the permanent magnets 18 under load. One possible way involves embedding in a mechanically resilient, non-magnetic support material such as titanium. This variant is preferred in those cases where the permanent magnets 18 are composed of Halbach magnets. Another embodiment of the invention involves integration of a tear-resistant and heat-resistant woven fabric, such as Kevlar or Teflon fiber, in the permanent magnets 18 during sintering thereof, which fabric is capable of absorbing tensile and compressive stress. If the permanent magnets 18 should break nevertheless, the resulting fragments will be held together by the woven fabric. In another embodiment the permanent magnets 18 are produced from a large number of small magnetic microcrystallites held together by the woven fabric.

In addition, the object of the invention is accomplished by providing a prosthesis which comprises a condyle 10 and a socket 12 of complementary spatial shape, separated by a gap 24, and a collar 14 arranged on the side of condyle 10 facing away from the socket 12, said condyle 10 and socket 12 each comprising a permanent magnet layer 18 and a shielding layer 20, and said permanent magnet layers 18 of condyle 10 and socket 12 having like polarity.

Surprisingly, it was found that the magnetic fields of condyle 10 and socket 12 can also be dimensioned in such a way that the resulting gap 24 will not correlate with an unnatural joint dilatation. As a result of the existing static load and tension of the muscles surrounding and fixing the joint, there is little or no contact between the condyle 10 and the collar 14. Consequently, friction between condyle 10 and collar 14 is only possible in a completely relaxed state, e.g. during sleep, or in case of strain associated with stretching of the joint. In such cases, the collar 14 advantageously functions as a mechanical barrier. The collar 14 must have properties as described above for the contact layer 16 in the present specification, in particular good body compatibility and high abrasion resistance, the latter property being essential only in the region of the bearing surface. That is, the collar 14 is formed at least partially, preferably completely, as contact layer 16, the preferred materials of which are plastics, such as polyethylene plastics, or ceramics. However, this collar 14 has no magnetic properties.

Moreover, the above teaching of the invention relating to the prosthesis with a collar 14 comprising a permanent magnet layer 18, a shielding layer 20 and a support layer 22 and embodiments thereof are valid and, if deemed reasonable, applicable without restrictions to a prosthesis with a non-magnetic collar 14 comprising a contact layer 16.

Therefore, as part of the present invention, there is provided for the first time a prosthesis for replacing a bone junction which addresses a magnetic and thus contactless joint guiding, so that levitation of the condyle 10 is present both in the state of rest and under load. In principle, the magnetic bearing is ideal for prosthetic maintenance of joints of any type, especially for hip, shoulder and knee prostheses and intervertebral disc prostheses. Loosening occurring e.g. in conventional hip prostheses at the junctions between prosthesis and hip or thigh bones, fastened using bone cement among other things, is significantly reduced as a result of magnetic damping. The components of the joint prostheses involve the outstanding feature of a layered structure of different materials, so that—apart from their magnetic properties—they comply with the resulting requirements of a body-compatible and abrasion-resistant coating and mechanical stability. Moreover, the massive and multilayer magnetic shielding advantageously achieves residual magnetic fields in the body of a patient that are well below the limit recommended by the Bundesamt für Strahlenschutz.

Another object of the invention is a method for replacing a bone junction in a mammal by fastening the condyle 10 of a prosthesis to an articular bone of the mammal, the socket 12 of the prosthesis with a shape complementary to that of condyle 10 to another articular bone of the mammal, and a collar 14 of the prosthesis to the socket 12 or a part of the mammal, said condyle 10, socket 12 and collar 14 each having at least one permanent magnet layer 18 and a shielding layer 20, the permanent magnet layers 18 of condyle 10, socket 12 and collar 14 being provided with like polarity, and the permanent magnet layers 18 being configured in such a way that repulsive magnetic forces produce a gap 24 between the contact layers 16 of condyle 10 and socket 12 and of condyle 10 and collar 14 when articular bone and prosthesis are under load.

In a preferred embodiment of the method according to the invention, replacement is effected in human bone junctions.

It will be appreciated that an existing bone junction must be removed first in order to create a cavity for the prosthesis. Both removal and implantation of the prosthesis are performed in a surgical procedure in accordance with customary medical practice. Fastening the prosthesis to the interfaces of articular bone and condyle 10 or socket 12 can be effected using e.g. bone cement. As an alternative to cementing, the socket 12 can also be held by a rough surface which is pressed in, i.e. so-called press-fit sockets. The magnetic fields generated by the permanent magnet layers 18 are adjusted in such a way that the depth of gap 24 is 1 to 10 mm, preferably 1 to 3 mm.

The prosthesis can be either delivered as an assembly previously prepared outside of the body or assembled in situ during surgery to meet the particular needs of a patient, as presently preferred in practice. Accordingly, the present invention is intended for use with both prefabricated joint prostheses, e.g. dual condyle prostheses on the hip joint, or intervertebral disc prostheses, and joint replacements individually adapted by the surgeon. In the case of previous assembly, at least the condyle 10 and the socket 12 of the prosthesis will be mounted outside of the mammal. In one embodiment of the method it is preferred that the collar 14 be fastened mechanically to the socket 12 so as to allow complete assembly of the prosthesis prior to surgery. In one embodiment of the present method, complete assembly of the prosthesis does, however, not include magnetization of the permanent magnet layer 18, which preferably is effected only in situ. That is, following implantation of the prosthesis, the permanent magnet layer 18 is exposed to an electric field, for example, so that magnetization takes place inside the body of the mammal. The shielding layer 20 of socket 12 preferably effects incomplete shielding of the permanent magnet layer 18 of socket 12, so that the healing process is stimulated.

The above teaching of the invention relating to the prosthesis and embodiments thereof are valid and, if deemed reasonable, applicable without restrictions to the method for replacing a bone junction of a mammal.

It will be appreciated that this invention is not restricted to the specific methods, devices and conditions as described herein, because such things may vary. It will also be appreciated that the terminology used herein solely serves the purpose of describing particular embodiments and is not intended to limit the protective scope of the invention. As used in the present specification and in the appended claims, singular word forms such as "a" or "the" encompass the corresponding plural forms unless the context unambiguously dictates otherwise. For example, reference to "a gap" includes a single gap or a plurality of gaps which can be identical or different, or, reference to "a method" includes equivalent steps and methods well-known to those skilled in the art.

With reference to a non-limiting example of specific embodiments, the invention will be illustrated in more detail below.

FIG. 1 shows a schematic drawing of a hip joint prosthesis.

The socket 12 and the collar 14 have a spherical convex shape, and the condyle 10 has a spherical concave shape, i.e., the geometric shape of socket 12 and collar 14 corresponds to the segment of a spherical shell, while the condyle 10 has the shape of a fitting spherical segment. The collar 14 is constituted of a plurality of spherical shell segments.

Figure 2:
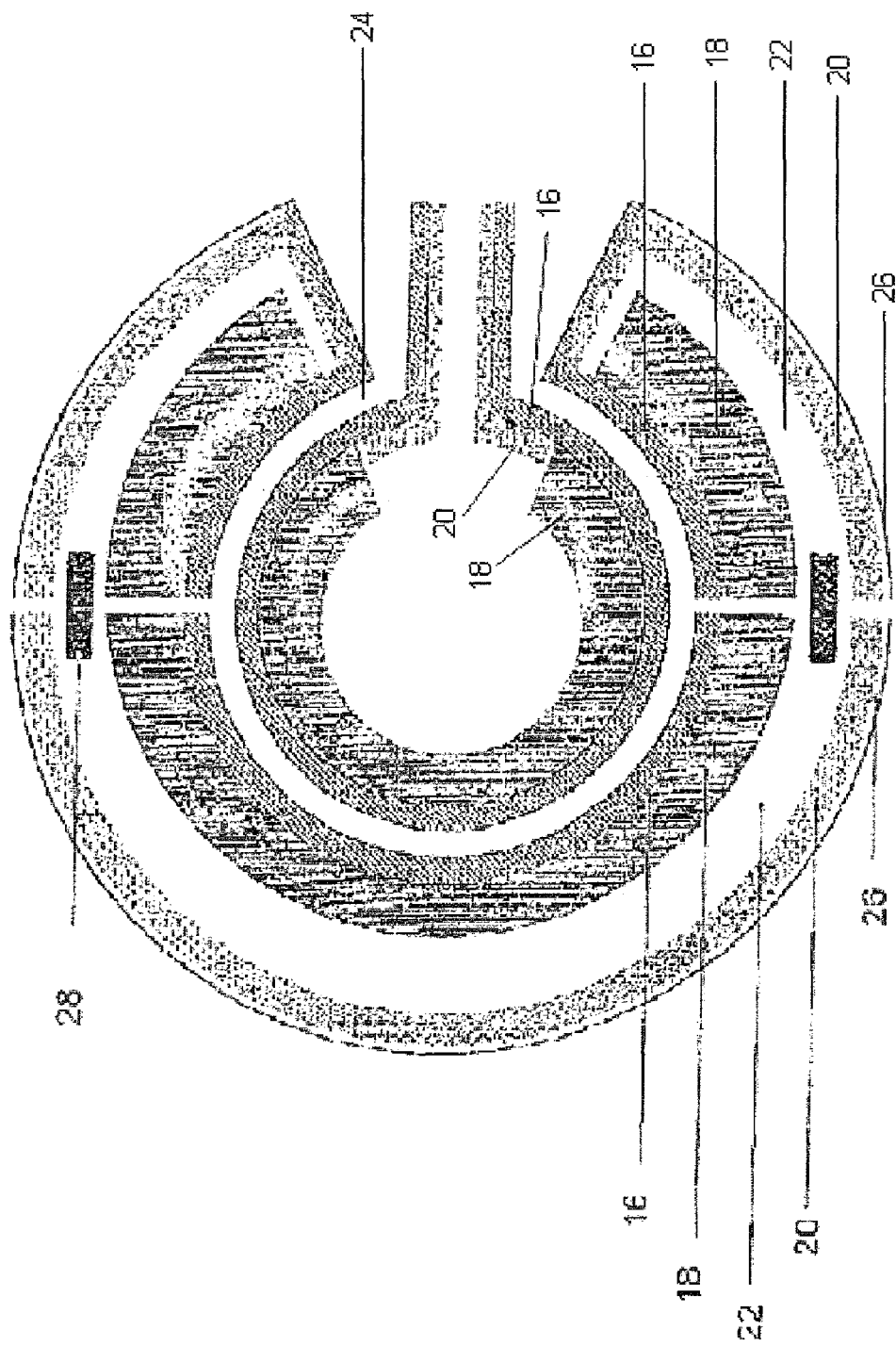

FIG. 2 shows a layer model of the hip joint prosthesis.

Condyle 10, socket 12 and collar 14 are constituted of a PE contact layer 16, a permanent magnet layer 18, a support layer 22, a shielding layer 20 and a body-compatible outer layer 26. The spherical shell segments of collar 14 are connected to the socket 12 by means of screw connections as mechanical connecting element 28. They are fabricated in such a way that the mobility of the joint is not influenced e.g. by jamming or blocking. Condyle 10 and collar 14 therefore have complementary shapes. In the region of the condyle 10, the support layer 22 continues on the shaft which is implanted into the thigh bone. In the region of the socket 12, the outer layer 26 makes contact with the hip bone.

Condyle 10, socket 12 and collar 14 have spherically convex or spherically concave permanent magnets 18 therein, i.e. the magnet 18 in condyle 10 has the shape of a sphere, while the magnets 18 in socket 12 and collar 14 are formed as a spherical shell. As a result of the equilibrium of repulsive magnetic forces of socket 12 and collar 14, a state of levitation (suspended state) of the condyle in the bearing is achieved. The level of required magnetic flux density B of the permanent magnets 18 is determined in the following calculation. The basis is the formula for calculating the magnetic bearing pressure $P_{mag}$ in cylindrical geometry:

$$P_{mag} = \tfrac{1}{2} \mu \cdot B^2,$$

where $\mu = 4\pi \cdot 10^{-7}$ Vs/Am represents the vacuum permeability in the joint gap and B represents the magnetic flux density.

The currently strongest commercially available permanent magnets 18 achieve long-term stable flux densities B on the surface of the magnets 18 of up to 1.0 Tesla. The maximum magnetic bearing pressures achievable in theory therefore amount to 400,000 N/m².

If the condyle has a radius r=0.03 m, and if the bearing surface is approximated by the lower half of a hemispherical shell, the relevant bearing surface is calculated to be A=0.003 m² according to the formula:

$$A = \tfrac{1}{4} \cdot 4\pi \cdot r^2$$

With a maximum possible bearing pressure of 400,000 N/m² and a bearing surface of 0.003 m², there results a theoretically possible maximum weight force of 1,200 N or a maximum load mass of 120 kg per hip joint prosthesis. Assuming an 80 kg weight patient, each hip prosthesis must bear a static load of 40 kg at maximum and has additional reserves to cushion peak loads up to three times as high (120 kg).

LIST OF REFERENCE NUMBERS

10 Condyle
12 Socket
14 Collar
16 Contact layer
18 Permanent magnet layer
20 Shielding layer
22 Support layer
24 Gap
26 Outer layer
28 Connecting element of socket 12 and collar 14

The invention claimed is:

1. A prosthesis for replacing a bone junction, said prosthesis comprising a condyle (10) and a socket (12) of complementary spatial shape and a collar (14), said condyle (10), socket (12) and collar (14) each comprising a permanent magnet layer (18) and a shielding layer (20), the condyle (10) and the socket (12) as well as the condyle (10) and the collar (14) being separated by a gap (24), said permanent magnet layers (18) of condyle (10), socket (12) and collar (14) having like polarity, the flux density of said permanent magnet layers (18) of condyle (10) and socket (12) being at least 0.4 Tesla, and the permanent magnet layer (18) of collar (14) having at most the flux density of the permanent magnet layers (18) of condyle (10) and socket (12).

2. The prosthesis according to claim 1, wherein the condyle (10), the socket (12) and/or the collar (14) have a contact layer (16) and/or a support layer (22).

3. The prosthesis according to claim 2, wherein, the socket (12) and/or the collar (14) have layer (16) and a layer (22), and wherein the contact layer (16), the permanent magnet layer (18), the support layer (22) and the shielding layer (20) are arranged in the order as mentioned.

4. The prosthesis according to claim 2, wherein the contact layer (16), the permanent magnet layer (18) and/or the shielding layer (20) simultaneously function as the support layer (22).

5. The prosthesis according to claim 2, wherein the permanent magnet layer (18), the shielding layer (20) and/or the support layer (22) simultaneously function as the contact layer (16).

6. The prosthesis according to claim 2, wherein the condyle (10), the socket (12) and/or the collar (14) have a contact layer (16), wherein the contact layer (16) comprises plastic, ceramic, steel or titanium.

7. The prosthesis according to claim 6, wherein the contact layer (16) comprises PE plastic or cobalt-chromium alloy.

8. The prosthesis according to claim 1, wherein the socket (12) and the collar (14) have a spherical concave shape and the condyle (10) has a convex spherical shape.

9. The prosthesis according to claim 1, wherein the collar (14) is arranged on a side of the condyle (10) facing away from the socket (12).

10. The prosthesis according to claim 1, wherein the socket (12) and the collar (14) are mechanically connected by means of a connecting element (28).

11. The prosthesis according to claim 1, wherein the condyle (10) and the collar (14) have complementary spatial shapes.

12. The prosthesis according claim 1, wherein the prosthesis has a maximum load limit which corresponds to at least 1.5 times the static load.

13. The prosthesis according to claim 1, wherein the permanent magnet layer (18) consists of a ceramic oxide material or a metal of subgroup VIII or an alloy thereof.

14. The prosthesis according to claim 13, wherein the permanent magnet layer (18) comprises a ceramic oxide material of barium oxide or iron oxide.

15. The prosthesis according to claim 13, wherein the permanent magnetic layer (18) comprises a metal of subgroup VIII being-iron, cobalt or nickel.

16. The prosthesis according to claim 13, wherein the permanent magnet layer (18) comprises an alloy of said subgroup VIII metal being an alloy among iron, cobalt or nickel, or an alloy thereof with platinum or rare earths.

17. The prosthesis according to claim 16, wherein the alloy of said subgroup VIII metal is a neodymium-iron-boron alloy or a cobalt-samarium alloy.

18. The prosthesis according to claim 1, wherein the shielding layer (20) effects shielding of the magnetic field of the permanent magnet layer (18) on the side facing away from the gap (24) by a factor of at least 1,000.

19. The prosthesis according to claim 1, wherein the shielding layer (20) comprises a magnetically soft material and/or a magnet with a polarity opposite to that of the permanent magnet layer (18).

20. The prosthesis according to claim 19, wherein the shielding layer (20) comprises a magnetically soft material chosen from the group consisting of structural steel, iron, nickel, cobalt, mu-metal and a combination thereof.

21. The prosthesis according to claim 1, wherein the support layer (22) consists of titanium, alloys thereof, or a woven fabric.

22. A method for replacing a bone junction in a mammal by fastening a condyle (10) of a prosthesis to an articular bone of the mammal, a socket (12) of the prosthesis with a shape complementary to that of condyle (10) to another articular bone of the mammal, and a collar (14) of the prosthesis to the socket (12) or a part of the mammal, said condyle (10), socket (12) and collar (14) each having a permanent magnet layer (18) and a shielding layer (20), the permanent magnet layers (18) of condyle (10), socket (12) and collar (14) being provided with like polarity and configured in such a way that repulsive magnetic forces produce a gap (24) between the condyle (10) and the socket (12) and between the condyle (10) and collar (14) when articular bone and prosthesis are under load.

23. The method according to claim 22, wherein at least the condyle (10) and the socket (12) of the prosthesis are assembled outside of the mammal.

24. The method according to claim 22, wherein the collar (14) is fastened mechanically to the socket (12) using a connecting element (28).

25. The method according to claim 22, wherein the gap (24) is caused to have a depth of from 1 to 10 mm.

26. The method according to claim 22, wherein the permanent magnet layer (18) is magnetized in situ.

27. The method according to claim 22, wherein the shielding layer (20) of the socket (12) effects incomplete shielding of the permanent magnet layer (18) of the socket (12).

* * * * *